United States Patent [19]

Gitlitz et al.

[11] 4,191,698

[45] Mar. 4, 1980

[54] TRICYCLOPENTYLTIN FLUORIDE

[76] Inventors: Melvin H. Gitlitz, Edison; John E. Engelhart, Westfield, both of N.J.

[21] Appl. No.: 853,338

[22] Filed: Nov. 21, 1977

Related U.S. Application Data

[63] Continuation-in-part of Ser. No. 780,049, Mar. 22, 1977, abandoned, which is a continuation-in-part of Ser. No. 715,114, Aug. 17, 1976, abandoned.

[51] Int. Cl.$^2$ ............................................... C07F 7/22
[52] U.S. Cl. .................................... 260/429.7; 424/288
[58] Field of Search .................................... 260/429.7

[56] References Cited

U.S. PATENT DOCUMENTS

| | | | |
|---|---|---|---|
| 3,070,615 | 12/1962 | Seyferth | 260/429.7 |
| 3,400,201 | 9/1968 | Mocotte | 260/429.7 X |
| 3,634,442 | 1/1972 | Seltzer | 260/429.7 X |

Primary Examiner—Helen M. S. Sneed
Attorney, Agent, or Firm—Kenneth G. Wheeless; Robert Spector

[57] ABSTRACT

Tricyclopentyltin fluoride effectively controls plant fungi and various types of insects when incorporated into formulations that are applied directly to these organisms or to substrates, including living plants, that are susceptible to infestation with these types of organisms. This compound is particularly advantageous due to its broader activity spectrum and considerably lower phytotoxicity relative to other tricyclopentyltin compounds.

1 Claim, No Drawings

TRICYCLOPENTYLTIN FLUORIDE

BACKGROUND OF THE INVENTION

This application is a continuation-in-part of Application Ser. No. 780,049, filed on Mar. 22, 1977, now abandoned, which is, in turn, a continuation-in-part of application Ser. No. 715,114, filed on Aug. 17, 1976, now abandoned.

This invention relates to compositions for selectively controlling fungi and pestiferous insects, including mites, using a novel tricyclopentyltin compound. The organisms against which the present compound is effective are responsible for a considerable portion of the annual damage to agricultural crops. Many trialkyltin compounds effectively control these organisms, however, these compounds are sufficiently non-selective toward desirable plant crops in that while the fungus or insect attacking the plant may be controlled, any plant to which the organotin compound is applied may be killed or severly damaged.

It is therefore an objective of this invention to provide a triorganotin compound that can effectively control a broad spectrum of fungi and insects on living plants without significantly damaging the plant. Many triorganotin compounds are active against either fungi or insects but not both classes of organisms. Surprisingly it has been found that tricyclopentyltin fluoride is unique among tricyclopentyltin compounds in achieving this objective.

SUMMARY OF THE INVENTION

This invention provides a novel triorganotin compound, tricyclopentyltin fluoride, and relatively non-phytotoxic compositions containing an insecticidally or fungicidally effective amount of this organotin compound. An inert, non-phytotoxic liquid or solid diluent constitutes the major portion of said compositions.

DETAILED DESCRIPTION OF THE INVENTION

Tricyclopentyltin fluoride is conveniently prepared by reacting a tricyclopentyltin halide such as the chloride or bromide with an alkali metal fluoride, such as potassium fluoride or hydrofluoric acid. Methods for preparing triorganotin halides, including tricyclopentyltin halides, are well known and do not form part of the present invention. Alternatively, a tricyclopentyltin halide such as the chloride, bromide or iodide, can be converted to tricyclopentyltin hydroxide or bis[(tricyclopentyl)tin] oxide by hydrolysis using an alkali metal hydroxide in a liquid medium that will dissolve the tricyclopentyltin halide but not the final product. The hydroxide or oxide is then reacted with hydrofluoric acid to form the corresponding fluoride.

Tricyclopentyltin halides wherein the halogen is chlorine, bromine or iodine can be prepared by reacting at least three moles of the corresponding cyclopentyl or cyclopentylalkyl magnesium halide, $CypMgZ^1$, wherein Cyp represents a cyclopentyl ring, for every mole of an alkyltin trihalide $R^3SnZ_3^2$ wherein $R^3$ is lower alkyl and preferably contains from 1 to 4 carbon atoms. The resultant tetraorganotin compound, $Cyp_3SnR^3$, is reacted with an equimolar amount of a stannic halide, $SnZ_4^3$. During the reaction the lower alkyl group $R^3$ present on the tetraorganotin compound is replaced by a halogen atom from the stannic halide. The reactions involved in the formation of tricyclopentyltin halides can be represented by the following two equations where $Z^1$, $Z^2$ and $Z^3$ are individually selected from the group consisting of chlorine, bromine and iodine.

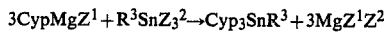

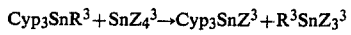

The aforementioned alkyltin trihalide $R^3SnZ_3^2$ can, in turn, be prepared by reacting the corresponding alkyl halide, $R^3Z^2$, with a stannous halide $SnZ_2^2$ as described in U.S. Pat. No. 3,340,283, the pertinent sections of which are hereby incorporated by reference.

The reaction between the stannic halide and tetraorganotin compound should be performed under anhydrous conditions at temperatures from about $-25°$ to $80°$ C., preferably from $+25°$ to $80°$ C., in a hydrocarbon solvent. Preferred solvents include pentane, hexane and cyclohexane.

Preferably the stannic halide is dissolved in an organic solvent and the resultant solution added dropwise to a second solution containing the tetraorganotin compound in the same solvent. The temperature of the reaction mixture is preferably maintained below about $30°$ C. during the addition, which requires about one hour, after which the mixture is heated to a temperature from $35°$ to $80°$ C. Preferably the temperature employed is the reflux temperature of the reaction mixture. Heating is continued for from about 15 to 60 minutes to ensure complete reaction. The reaction mixture is then allowed to cool to ambient temperature, and extracted with one or more portions of water or aqueous mineral acid. The by-product of the reaction, a monoorganotin trihalide, $R^3SnZ_3^3$, is soluble in the aqueous phase of the reaction mixture. The desired product remains in the organic phase, and is readily isolated by boiling off the hydrocarbon solvent. No further purification is usually required, however the product can be distilled if desired. The organic layer is preferably freed of any dissolved water following the extracting step. Any of the conventional chemical dehydrating agents are suitable, provided that they will not react with either the triorganotin halide or the hydrocarbon solvent. Preferred drying agents include anhydrous magnesium sulfate, anhydrous sodium sulfate and anhydrous calcium sulfate.

Tricyclopentyltin fluoride effectively controls many types of undesirable fungi, insects and mites, when applied to living plants that are susceptible to infestations of these organisms. A single application of this compound to living plants or other substrates provides residual and extended control of many varieties of fungi and insects for a considerable period of time, the duration of which is dependent to some extent upon mechanical and biological influences, including weather. The combination of fungicidal, miticidal and insecticidal activity is not common for a single organotin compound. Formulations containing tricyclopentyltin fluoride can also be applied directly onto the organism to be controlled.

The minimum concentration of tricyclopentyltin fluoride that is effective against a given fungus, mite, or insect dependent upon whether the organism is contacted with, or, as in the case of insects and mites, ingests the toxicant. The weight of compound constituting an effective dose is also dependent upon the susceptibility of the particular organism to a given triorganotin compound. For control of mites, good results are obtained with liquid or dust compositions containing as little as two parts per million by weight of toxicant. Compositions containing up to 90 percent by weight of toxicant can be employed to treat a heavily infested area.

In the preparation of dust compositions, tricyclopentyltin fluoride can be blended with many commonly employed finely divided solid carriers such as fuller's earth, attapulgite, bentonite, pyrophyllite, vermiculite, diatomaceous earth, talc, chalk, gypsum and wood flour. The carrier, usually in a finely divided form, is ground or mixed with the toxicant or wetted with a dispersion of the toxicant in a volatile liquid. Depending upon the relative proportions of toxicant and carrier, these compositions can be employed as concentrates that are subsequently diluted with additional solid carrier to obtain the desired amount of active ingredient. Alternatively, such concentrate dust compositions can be employed in combination with various known anionic, cationic or non-ionic surfactants as emulsifying or dispersing agents to form spray concentrates. Such concentrates are readily dispersible in liquid carriers to form spray compositions or liquid formulations containing the toxicants in any desired amount. The choice and concentration of surfactant are determined by the ability of the material to facilitate the dispersing of the concentrate in the liquid carrier to produce the desired liquid composition. Suitable liquid carriers include water, methanol, ethanol, isopropanol, methyl ethyl ketone, acetone, methylene chloride, chlorobenzene, toluene, xylene and petroleum distillates. Among the preferred petrolleum distillates are those boiling under 400° F. at atmospheric pressure and having a flash point above about 80° F.

When operating in accordance with the present invention, tricyclopentyltin fluoride or a composition containing this compound can be applied directly onto the organism to be controlled or to the site to be protected, particularly plants and trees. Application to the foliage of plants is conveniently carried out using power dusters, boom sprayers and spray dusters. When employed in this manner the compositions should not contain any significant amounts of phytotoxic diluents. In large scale operations, dusts or low volume sprays may be applied from an aircraft.

The following examples represent preferred embodiments of compositions containing tricyclopentyltin fluoride and the use of these compositions as fungicides and insecticides. The examples are not intended to limit the scope of the accompanying claims. All parts and percentages are by weight unless otherwise specified.

EXAMPLES

EXAMPLE 1—Preparation of Tricyclopentyltin Fluoride

A. Preparation of Butyltricyclopentyltin

To 24.3 g (1 g atom) of magnesium chips heated to a temperature of 40° C. under a nitrogen atmosphere was added a 25 cc portion of a solution containing 149 g (1 mole) of bromocyclopentane dissolved in 750 cc of anhydrous tetrahydrofuran. The reaction was initiated using a few drops of ethylene dibromide. The remaining portion of the bromocyclopentane solution was gradually added during a period of 2 hours while the reaction mixture was heated to the boiling point. The reaction mixture was allowed to cool to ambient temperature and remain at this temperature for about 16 hours, during which time stirring of the mixture was continued. At the end of this period all of the magnesium appeared to have reacted. A 500 cc portion of this solution containing 0.66 mole of cyclopentyl magnesium bromide was added dropwise to a stirred solution of butyltin trichloride (56.4 g, 0.2 mole) dissolved in 250 cc of dry benzene. The addition required one hour and was conducted under a nitrogen atmosphere. During the addition the temperature of the reaction mixture was maintained below 45° C. Following completion of the addition the reaction mixture was heated to the boiling point for one hour, then allowed to cool to ambient temperature and stirred for 18 hours. To the resultant mixture was added a solution containing 200 cc water and 35 g of citric acid. The organic phase of the resultant two phase liquid was separated and the water present therein removed using a portion of anhydrous magnesium sulfate, which was subsequently removed by filtration. The solvent was evaporated under reduced pressure to yield 72.25 g (94% yield) of a liquid, butyltricyclopentyltin, exhibiting a refractive index ($\eta_D^{27°\ C.}$) of 1.5220. This liquid was extracted once with methanol. Analysis by vapor phase chromatography indicated that the product was 96.7% pure. The product was found to contain 30.24% tin. The calculated value for butyltricyclopentyltin is 30.98%.

B. Cleavage of Butyltricyclopentyltin to Tricyclopentyltin Chloride

A 19.2 g (0.05 mole) portion of the butyltricyclopentyltin prepared as described in part A of this example was dissolved in 75 cc of heptane. To this solution was added a solution containing 13.0 g (0.05 mole) of anhydrous stannic chloride and 75 cc heptane. The addition required 20 minutes, following which the resultant mixture was heated to the boiling point for 30 minutes and then allowed to cool to ambient temperature. A solution obtained by combining 4 cc of 12 N aqueous hydrochloric acid and 96 cc water was then added to the reaction mixture with vigorous stirring both during the addition and for five minutes thereafter. The organic layer of the resultant two-phase liquid was combined with an aqueous hydrochloric acid solution prepared as described hereinabove. The organic layer was isolated and the water therein removed using a quantity of anhydrous magnesium sulfate. The heptane was then evaporated under reduced pressure to yield 17.8 g of pale yellow crystals exhibiting a melting range of 41°-44° C. Upon analysis by vapor phase chromatography the product was found to be 97.2% pure. Following a recrystalization from pentane at −78° C., the product melted between 44° and 45° C. and was 99.6% pure, as determined by vapor phase chromatography.

C. Conversion of Tricyclopentyltin Chloride to the Corresponding Hydroxide

Tricyclopentyltin hydroxide was prepared by adding a solution of the corresponding chloride (18.1 g of the chloride in 40 cc of tetrahydrofuran) to a solution containing 3.0 g of sodium hydroxide, 12 cc water and 12 cc methanol. The addition was gradual and required 20 minutes, at which time 12 cc of water were added. The resultant slurry was stirred for 0.5 hour, at which time 150 cc of water were added to completely precipitate the product. The solid was isolated and washed with deionized water until no detectible amount of chloride ion was present in the water. The solid was then dried in a circulating air oven maintained at a temperature of 40° C. Analysis by potentiometric titration indicated that the hydroxide was between 98.6 and 99.1% pure.

D. Conversion of Tricyclopentyltin Hydroxide to Tricyclopentyltin Fluoride

A solution containing 300 g. of tricyclopentyltin hydroxide and 3600 cc of tetrahydrofuran was clarified by filtration. To this solution was gradually added a solution obtained by combining 50 g of a 48% aqueous hydrofluoric acid solution with 150 cc of water. The resultant mixture, which contained a white precipitate, was heated to the boiling point (64° C.) for 0.25 hour, then cooled to ambient temperature filtered, and washed sequentially with 1 liter of a 0.1% aqueous hydrofluoric acid solution, 1 liter deionized water and 500 cc methanol. After being dried under reduced pressure at a temperature of 50° C. the white solid (280 g) melted from 275° to 280° C. with evidence of decomposition. The solid was found to contain 34.05% tin and 5.32% fluorine. The calculated values for tricyclopentyltin fluoride are 34.40% tin and 5.51% fluorine.

The efficacy of tricyclopentyltin fluoride as a control agent for three different plant fungi (grape downy mildew, apple powdery mildew and wheat leaf rust) was evaluated and compared with the performance of several other tricyclopentyltin compounds. The results of this evaluation are disclosed in the following tables 2, 3 and 4. The phytotoxicity of the various compounds tested was also evaluated at various concentration levels. These data appear in tables 5, 6 and 7. Quantitative ratings for phytotoxicity are given in each of the first three tables. A rating of 0 indicates no phytotoxicity. A rating of 1 indicates that the degree of phytotoxicity was sufficient to make the plant commercially worthless. A rating of 2 indicates that the plant was killed.

Biological Activity and Phytotoxicity of Tricyclopentyltin Fluoride Relative to Other Triorganotin Compounds The following procedures were employed to evaluate the efficacy tricyclopentyltin fluoride and other compounds as control agents for a number of representative fungi and insects.

PROCEDURE 1—Employed Using Two-spotted Spider Mite (*Tetranychus urticae*) and Cabbage Looper (*Trichoplusia ni*)

A cotton plant with two fully expanded leaves is dipped into an aqueous dispersion of the test compound. An additional portion is injected into the soil at the root zone. Larvae of the cabbage looper are dipped into the same dispersion and placed in petri dish cages clamped around the treated foliage. When using the two-spotted spider mite as the test organism the leaves of the plant are infested with mites before the plant is treated with the organotin compound. A mortality count is taken six days after treatment.

PROCEDURE 2—Employed Using Codling Moth Larvae To Determine Ovicidal Activity And Control Of Newly Hatched Larvae The test chemical is dissolved or dispersed in a small amount of a suitable water-miscible solvent and diluted with water to achieve the desired concentration. The resultant composition is applied to apples or pears which are then covered with eggs of the codling moth. The fruit is then incubated for from eight to ten days in a greenhouse. The number of living and dead larvae are then counted and compared with a sample of untreated fruit used as a control.

PROCEDURE 3—Employed Using Grape Downy Mildew (*Plasmopara viticola*), Wheat Leaf Rust (*Puccinia recondita*) and Apple Powdery Mildew (*Podosphaera leucotricha*)

Host plants, (grape, wheat or apple, depending upon the fungus) are sprayed with a water suspension of the test compound and then inoculated with the pathogen. A number of control plants that have not been sprayed are also inoculated. After disease symptoms are well developed on the untreated control plants the test plants are graded for disease control.

TABLE 1
Activity of Tricyclopentyltin Fluoride As An Insecticide

| Organism | Proc. No. | Concentration (ppm.) | Control Rating (%) |
|---|---|---|---|
| Spider Mite | 1 | 400 | 99 |
|  |  | 100 | 97 |
| Cabbage Looper | 1 | 400 | 100 |
| Codling Moth Larvae | 2 | 400 | 100 |

TABLE 2
Efficacy of Various Triorganotin Compounds Against Grape Downy Mildew

| Compound | Concentration (ppm.) | % Control | Phytotoxicity |
|---|---|---|---|
| Tricyclopentyltin fluoride | 300 | 95 | 0 |
|  | 75 | 93 | 0 |
| Tricyclopentyltin hydroxide (control) | 300 | 93 | 1 |
|  | 75 | 83 | 0 |
| Tricyclopentyltin benzoate (control) | 300 | 75 | 1 |
|  | 75 | 50 | 0 |
| Triphenyltin hydroxide (control) | 300 | 100 | 1 |
|  | 75 | 95 | 1 |

Of the four compounds tested only tricyclopentyltin fluoride did not produce any phytotoxic effects at a concentration of 300 parts per million (ppm.). The control rating of the fluoride at a concentration of 75 ppm. was higher than the two other tricyclopentyltin compounds. Triphenyltin hydroxide had a higher control rating at this level, but was too phytotoxic to be commercially useful.

TABLE 3
Efficacy of Various Triorganotin Compounds Against Apple Powdery Mildew

| Compound | Concentration (ppm.) | % Control |
|---|---|---|
| Tricyclopentyltin fluoride | 300 | 93 |
|  | 75 | 90 |
| Tricyclopentyltin phenoxide (control) | 300 | 83 |
|  | 75 | 50 |
| Tricyclopentyltin acetate (control) | 75 | 25 |
| Triphenyltin hydroxide (control) | 75 | 25 |

At a concentration of 75 ppm. the efficacy of tricyclopentyltin fluoride was considerably higher than the other compounds tested. A control rating of 50% or less is not considered commercially significant. None of the compounds tested were phytotoxic.

TABLE 4

Efficacy of Various Triorganotin Compounds Against Wheat Leaf Rust at 300 ppm.

| Compound | % Control | Phytotoxicity |
|---|---|---|
| Tricyclopentyltin fluoride | 90 | 0 |
| Tricyclopentyltin hydroxide (control) | 25 | 0 |
| Tricyclopentyltin chloride (control) | 25 | 2 |
| Triphenyltin hydroxide (control) | 25 | 0 |

Of the four compounds tested only tricyclopentyltin fluoride effectively controlled wheat leaf rust. These data demonstrate a wider spectrum of activity for tricyclopentyltin fluoride relative to other tricyclopentyltin or triphenyltin compounds that are useful plant fungicides.

The phytotoxicity of a number of tricyclopentyltin compounds and triphenyltin hydroxide on grape vines, wheat and barley was evaluated quantitatively using the following scale:

0 = no phytotoxicity

1 = very slight injury, the minimum that could be observed

2 = less than 10% of leaf surface injured

3 = 10-50% of leaf surface injured

4 = 50-90% of leaf surface injured

5 = plant killed

If the rating was considered to be somewhere between two integers based on observations of other plants, the lower integer followed by "0.5" was employed as the rating.

TABLE 5

Phytotoxicity of Various Triorganotin Compounds Applied to Grape Vines

| Compound | Phytotoxicity at Indicated Concentration (ppm.) | | |
|---|---|---|---|
| | 1200 | 300 | 75 |
| Tricyclopentyltin fluoride | 3.5 | 1.5 | 0 |
| Tricyclopentyltin hydroxide (control) | 4.5 | 2.5 | 1 |
| Tricyclopentyltin acetate (control) | 5 | 4 | 2 |
| Triphenyltin hydroxide (control) | 5 | 3.5 | 2.5 |

TABLE 6

Phytotoxicity of Various Triorganotin Compounds Applied to Wheat

| Compound | Phytotoxicity at Indicated Concentration (ppm.) | | |
|---|---|---|---|
| | 1200 | 300 | 75 |
| Tricyclopentyltin fluoride | 1.5 | 0 | 0 |
| Tricyclopentyltin hydroxide (control) | 2.5 | 1 | 0 |
| Tricyclopentyltin chloride (control) | 5 | 3 | 1 |

TABLE 7

Phytotoxicity of Various Triorganotin Compounds Applied to Barley

| Compound | Phytotoxicity at Indicated Concentration (ppm.) | | |
|---|---|---|---|
| | 600 | 150 | 38 |
| Tricyclopentyltin fluoride | 2 | 1 | 0 |
| Tricyclopentyltin hydroxide (control) | 3.5 | 2 | 1 |
| Tricyclopentyltin acetate (control) | 3.5 | 2 | 1 |
| Triphenyltin hydroxide (control) | 4 | 3 | 1 |

The phytotoxicity values in the preceding three tables demonstrate that tricyclopentyltin fluoride is unique among the other triorganotin compounds tested by virtue of its being the least damaging to the plants. This is surprising and unexpected considering that this compound also exhibited the highest activity against representative plant fungi of all the compounds tested.

What is claimed is:

1. Tricyclopentyltin fluoride as a novel triorganotin compound.

* * * * *

UNITED STATES PATENT OFFICE
CERTIFICATE OF CORRECTION

Patent No. 4,191,698　　　　　Dated March 4, 1980

Inventor(s) Melvin H. Gitlitz and John E. Engelhart

It is certified that error appears in the above-identified patent and that said Letters Patent are hereby corrected as shown below:

Title Page: Immediately following the names of the inventors insert

--Assignee: M&T Chemicals Inc., Stamford, Conn.

Signed and Sealed this

Twelfth Day of August 1980

[SEAL]

*Attest:*

SIDNEY A. DIAMOND

*Attesting Officer*　　　*Commissioner of Patents and Trademarks*